US010543028B2

(12) United States Patent
Isch (10) Patent No.: US 10,543,028 B2
(45) Date of Patent: Jan. 28, 2020

(54) ADJUSTABLE WEDGE (71) Applicant: Biomet Manufacturing, LLC, Warsaw, IN (US)

(72) Inventor: Bryce A. Isch, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 115 days.

(21) Appl. No.: 15/887,193

(22) Filed: Feb. 2, 2018

(65) Prior Publication Data

US 2018/0221071 A1 Aug. 9, 2018

Related U.S. Application Data (60) Provisional application No. 62/455,181, filed on Feb. 6, 2017.

(51) Int. Cl.
A61B 17/80 (2006.01)
A61F 2/42 (2006.01)
(Continued)

(52) U.S. Cl.
CPC .......... *A61B 17/8095* (2013.01); *A61F 2/28* (2013.01); *A61F 2/4202* (2013.01);
(Continued)

(58) Field of Classification Search
CPC ........ A61B 17/8095; A61F 2002/4217; A61F 2002/4223; A61F 2002/30281
See application file for complete search history.

(56) References Cited

U.S. PATENT DOCUMENTS 5,443,515 A * 8/1995 Cohen ................ A61F 2/44
606/247
5,776,197 A * 7/1998 Rabbe ................ A61B 17/70
606/247
(Continued)

FOREIGN PATENT DOCUMENTS

EP 1308135 5/2003
WO 2013075124 5/2013
WO 2018144818 8/2018

OTHER PUBLICATIONS

"International Application Serial No. PCT US2018 016592, International Search Report dated Apr. 18, 2018", 5 pgs.
(Continued)

Primary Examiner — David H Willse
Assistant Examiner — Javier G Blanco
(74) Attorney, Agent, or Firm — Schwegman Lundberg & Woessner, P.A.

(57) ABSTRACT

An adjustable wedge can be used in an Evans technique foot and ankle reconstructive wedge surgery. The adjustable wedge can include a slide. The slide can be positioned to a suitable location on a patient's calcaneus, then fastened to the calcaneus through first and second holes through the slide at opposite ends of the slide. The adjustable wedge can include a body having a pair of wedged surfaces configured to contact the cutout of the calcaneus. The body can include a slot extending between the wedged surfaces. The slot can be sized to accommodate the slide so that the slide is slidable within the slot. A circumferential surface can extend circumferentially between the wedged surfaces. A threaded hole can extend through the circumferential surface to the slot. The threaded hole can receive a fastener, such as a set screw, to secure the slide to the body.

14 Claims, 5 Drawing Sheets (51) Int. Cl.
*A61F 2/28* (2006.01)
*A61F 2/30* (2006.01)

(52) U.S. Cl.
CPC .............. *A61F 2002/30281* (2013.01); *A61F 2002/4217* (2013.01); *A61F 2002/4223* (2013.01)

(56) References Cited

U.S. PATENT DOCUMENTS

| | | | | |
|---|---|---|---|---|
| 7,309,358 B2* | 12/2007 | Berry | ............ | A61F 2/44 606/86 A |
| 2002/0116065 A1* | 8/2002 | Jackson | ............ | A61F 2/446 623/17.16 |
| 2005/0159813 A1* | 7/2005 | Molz, IV | ............ | A61F 2/447 623/17.11 |
| 2007/0038303 A1* | 2/2007 | Myerson | ............ | A61B 17/562 623/21.18 |
| 2009/0082770 A1* | 3/2009 | Worner | ............ | A61B 17/8061 606/60 |
| 2010/0004747 A1* | 1/2010 | Lin | ............ | A61B 17/7059 623/17.16 |
| 2012/0143336 A1* | 6/2012 | Aflatoon | ............ | A61F 2/4465 623/17.16 |
| 2012/0184959 A1 | 7/2012 | Price et al. | | |
| 2012/0197399 A1* | 8/2012 | Kirschman | ............ | A61B 17/7059 623/17.11 |
| 2013/0138154 A1* | 5/2013 | Reiley | ............ | A61B 17/8095 606/280 |
| 2014/0107786 A1* | 4/2014 | Geisler | ............ | A61F 2/30965 623/17.16 |
| 2015/0032220 A1 | 1/2015 | Tyber et al. | | |
| 2016/0000486 A1* | 1/2016 | Leduc | ............ | A61B 17/8095 606/297 |

OTHER PUBLICATIONS

"International Application Serial No. PCT US2018 016592, Written Opinion dated Apr. 18, 2018", 8 pgs.

* cited by examiner

ADJUSTABLE WEDGE

CLAIM OF PRIORITY

This application claims the benefit of priority to U.S. Provisional Application Ser. No. 62/455,181, filed on Feb. 6, 2017, which is incorporated herein by reference in its entirety.

FIELD OF THE DISCLOSURE

The present disclosure relates to an adjustable wedge suitable for use in an Evans technique foot and ankle reconstructive wedge surgery, as well as other techniques.

BACKGROUND OF THE DISCLOSURE

The Evans osteotomy is one of the most common procedures used to correct flatfoot deformity. This technique requires an osteotomy of the calcaneal neck followed by distraction, and then maintenance of distraction by interpositional bone graft or bone graft material.

SUMMARY

In one example of an adjustable wedge, a slide can include first and second holes through the slide at opposite ends of the slide. A body can have a pair of wedged surfaces that are angled with respect to each other. The body can have a slot extending through the body between the wedged surfaces. The slot can be sized to accommodate the slide so that the slide is slidable within the slot. The body can have a circumferential surface extending circumferentially between the wedged surfaces. The body can have a threaded hole extending through the circumferential surface to the slot. The threaded hole can receive a fastener, such as a set screw, to secure the slide to the body.

In another example of an adjustable wedge, a slide can extend along a first direction. The slide can including first and second holes extending through the slide at opposite ends of the slide. The first and second holes can extend in a second direction perpendicular to the first direction. The slide can extend between first and second enlarged longitudinal portions of the slide. The first and second enlarged longitudinal portions can surround the first and second holes, respectively. A body can have a pair of wedged surfaces that are angled with respect to each other. The pair of wedged surfaces can define respective planes that intersect outside the body along a line that defines a third direction. The third direction can be perpendicular to the first and second directions. A slot can extend through the body in the first direction between the wedged surfaces. The slot can be positioned proximate a widest portion of the circumferential surface. The slot can be sized to accommodate the slide so that the slide is slidable within the slot in the first direction. The slot can be sized smaller than the first and second enlarged longitudinal portions of the slide so that the first and second enlarged longitudinal portions prevent the slide from exiting the slot. The slide and the slot can be being shaped to prevent rotation of the slide about an axis parallel to the first direction. The body can have a circumferential surface extending circumferentially between the wedged surfaces. The body can have a threaded hole extending through the circumferential surface to the slot. The threaded hole can extend in the second direction. The threaded hole can receive a set screw to secure the slide to the body.

In an example of a method for implanting an adjustable wedge into a corresponding wedged cutout of bone on a patient's calcaneus, a body of the adjustable wedge can be placed into the corresponding wedged cutout of bone on the patient's calcaneus. The body can include a pair of wedged surfaces configured to contact the cutout of bone. The body can include a slot extending between the wedged surfaces in an anterior-posterior direction. The adjustable wedge can include a slide extending through the slot and slidable within the slot in the anterior-posterior direction. The slide can be positioned in the anterior-posterior direction on the calcaneus to locate a pair of specified screw fixation locations. A pair of locking screws can be screwed into the bone on the patient's calcaneus at the pair of specified screw fixation locations through first and second holes on the slide, respectively, to secure the slide to the calcaneus. A fastener, such as a set screw, can be inserted into a threaded hole extending through a portion of the body to secure the body to the slide.

BRIEF DESCRIPTION OF THE DRAWINGS

Corresponding reference characters indicate corresponding parts throughout the several views. Elements in the drawings are not necessarily drawn to scale. The configurations shown in the drawings are merely examples, and should not be construed as limiting the scope of the invention in any manner.

DETAILED DESCRIPTION

An adjustable wedge can be used in an Evans technique foot and ankle reconstructive wedge surgery. The adjustable wedge can include a slide. The slide can be positioned to a suitable location on a patient's calcaneus, then fastened to the calcaneus through first and second holes through the slide at opposite ends of the slide. The adjustable wedge can include a body having a pair of wedged surfaces configured to contact the cutout of the calcaneus. The body can include a slot extending between the wedged surfaces. The slot can be sized to accommodate the slide so that the slide is slidable within the slot. A circumferential surface can extend circumferentially between the wedged surfaces. A threaded hole can extend through the circumferential surface to the slot. The threaded hole can receive a fastener, such as a set screw, to secure the slide to the body.

Figure 1:
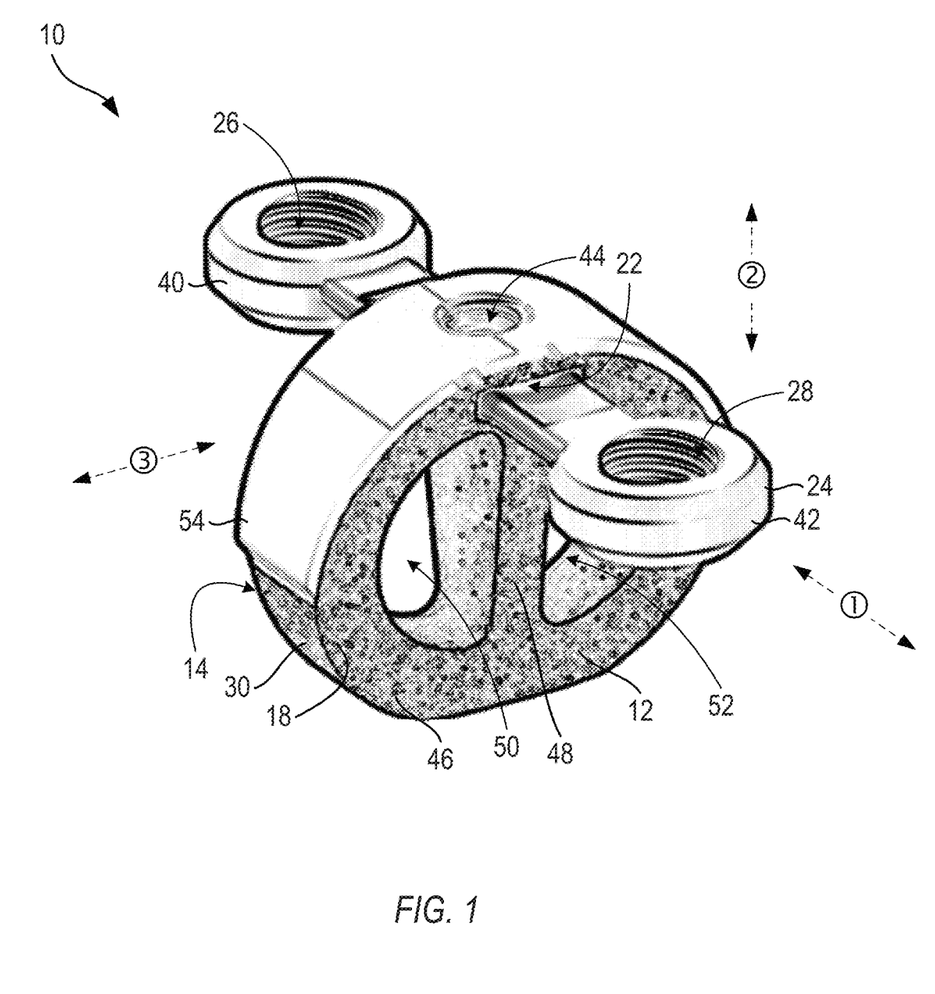
FIG. 1 shows a perspective view of an adjustable wedge, in accordance with some examples.
Figure 2:
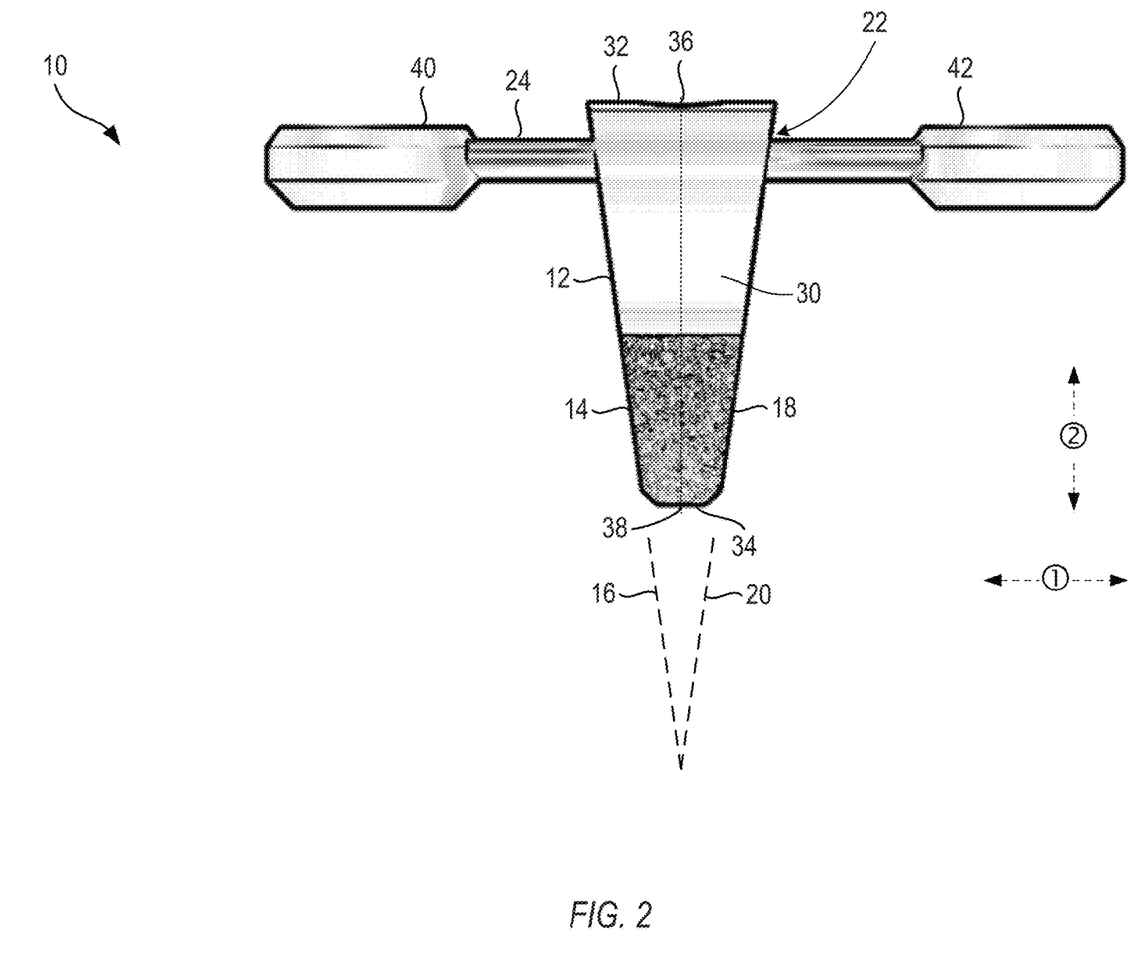
FIG. 2 shows a front view of the adjustable wedge of FIG. 1, in accordance with some examples.
Figure 3:
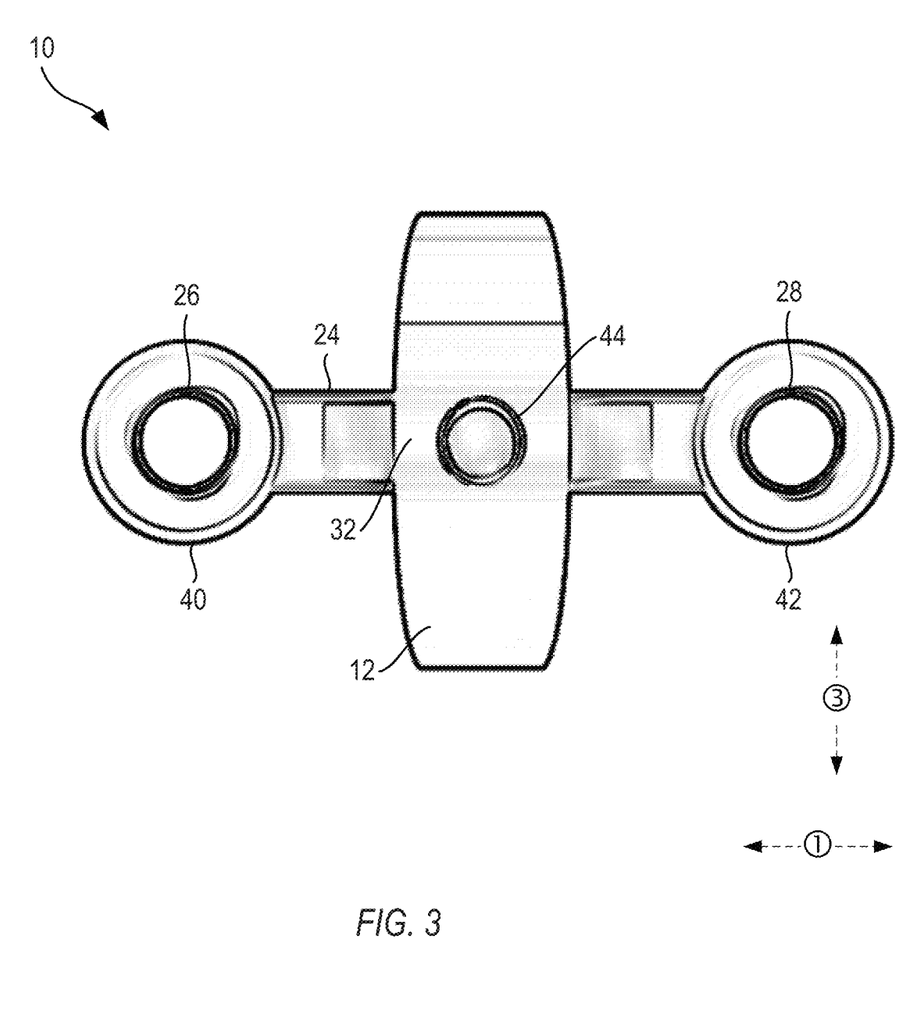
FIG. 3 shows a top view of the adjustable wedge of FIG. 1, in accordance with some examples.
Figure 4:
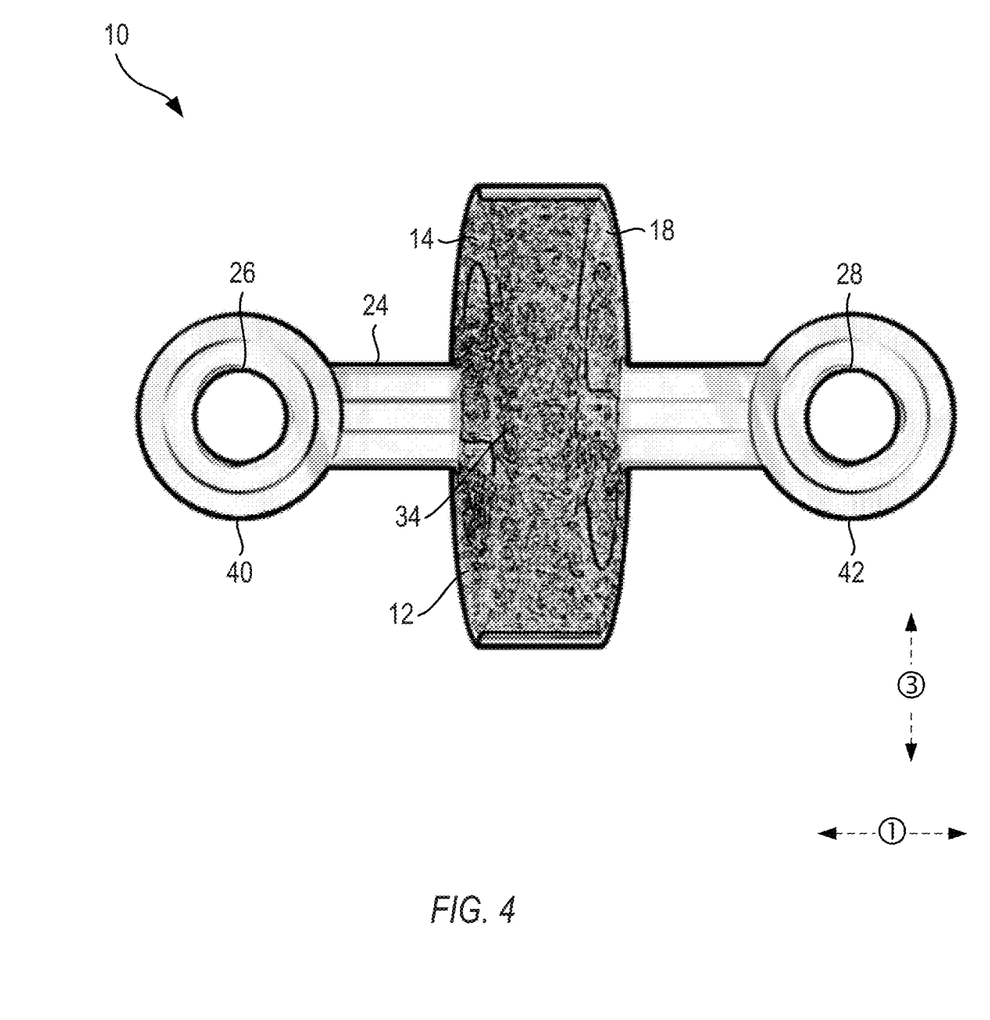
FIG. 4 shows a bottom view of the adjustable wedge of FIG. 1, in accordance with some examples.

FIG. 1 shows a perspective view of an adjustable wedge 10, in accordance with some examples. FIGS. 2-4 show respective side, top, and bottom views of the adjustable wedge 10 of FIG. 1, in accordance with some examples. The configuration shown in FIGS. 2-4 is but one example of an adjustable wedge 10. Other suitable configurations can also be used.

The adjustable wedge 10 can include a slide 24 extending along a first direction. In FIGS. 1-4, the first direction is indicated by an arrow labeled by a circled numeral 1.

In some examples, the slide 24 can include a first hole 26 and a second hole 28 extending through the slide 24 at opposite ends of the slide 24. In some examples, the first hole 26 and the second hole 28 can extend in a second direction. In FIGS. 1 and 2, the second direction is indicated by an arrow labeled by a circled numeral 2. In some examples, the second direction can be perpendicular to the first direction. In some examples, the first hole 26 and the second hole 28 can each be sized to accommodate a fastener such as a bone screw, so that two bone screws, when screwed into bone through the first hole 26 and the second hole 28, respectively, can secure the slide 24 to a specified location on the patient's calcaneus. In some examples, the first hole 26 and the second hole 28 can threaded. In some examples, the first hole 26 can have a first thread size and the second hole 28 can have a second thread size equal to the first thread size. In other examples, the two thread sizes can be different. In some examples, at least one of the first hole 26 and the second hole 28 can be a polyaxial hole configured to allow insertion of a bone screw in an "off-axis" manner.

In some examples, the slide 24 can extend between a first enlarged longitudinal portion 40 of the slide 24 and a second enlarged longitudinal portion 42 of the slide 24. In some examples, the first enlarged longitudinal portion 40 and the second enlarged longitudinal portion 42 can surround the first hole 26 and the second hole 28, respectively.

The adjustable wedge 10 can include a body 12. In some examples, the body 12 can be a wedge-shaped element that maintains the distraction of the calcaneal neck. In some examples, the body 12 can be formed from a rigid, biocompatible material, such as titanium or another suitable metal. In some examples, some or all of the body 12 can be formed with a textured surface, which can enhance bone growth around the body 12. In some examples, the body 12 can be formed to be porous, such as Trabecular Metal and OsseoTi Porous Metal, which are commercially available from Zimmer Inc. of Warsaw, Ind.

In some examples, the body 12 can be shaped so that opposing angled surfaces of the body 12 can make planar contact with respective surfaces of bone. Such planar contact can promote strength and comfort when the patient heals. The surfaces of the body 12 need not be perfectly smooth to form this planar contact. Rather, the surfaces can be roughened, or formed in a porous manner that produces rough surfaces. Such porosity or surface roughness can enhance bone growth over time, so that bone grows around and through the body 12, and strengthens the body 12 over time.

The body 12 can have a pair of wedged surfaces 14, 18 that are angled with respect to each other. In some examples, the pair of wedged surfaces 14, 18 can define respective planes 16, 20 that intersect outside the body 12 along a line that defines a third direction. In FIGS. 1, 3, and 4, the third direction (parallel to said line) is indicated by an arrow labeled by a circled numeral 3. In FIG. 2, said line would be perpendicular to the plane of the page at the intersection of planes 16 and 20, and is therefore not explicitly shown in FIG. 2. In some examples, the third direction can be perpendicular to the first and second directions.

In some examples, the body 12 can further include a circumferential surface 30 extending circumferentially between the wedged surfaces 14, 18. The circumferential surface 30 can have a widest portion 32 (FIG. 2) at which the wedged surfaces 14, 18 are positioned farthest from each other. The circumferential surface 30 can have a narrowest portion 34 (FIG. 2) at wedged surfaces 14, 18 are positioned closest to each other. In some examples, an axis extending from a midpoint 36 of the widest portion 32 to a midpoint 38 of the narrowest portion 34 can be aligned with the second direction.

In some examples, the body 12 can further include a slot 22 extending through the body 12 in the first direction between the wedged surfaces 14, 18. In some examples, the slot 22 can be positioned proximate the widest portion 32 of the circumferential surface 30, so that the slot 22 can be accessed from outside the bone. The slot 22 can be sized to accommodate the slide 24 so that the slide 24 is slidable within the slot 22. In some examples, the slide 24 is slidable within the slot 22 in the first direction. In some examples, the slot 22 can be sized smaller than the first enlarged longitudinal portion 40 and the second enlarged longitudinal portion 42 of the slide so that the first enlarged longitudinal portion 40 and the second enlarged longitudinal portion 42 prevent the slide 24 from exiting the slot 22. In some examples, the slide 24 and the slot 22 can be being shaped to prevent rotation of the slide 24 about an axis extending along the first direction. In some examples, the slide 24 and the slot 22 each include opposing walls that are flat. In some examples, the slot 22 can be straight, optionally with a uniform cross-section at each location along its length. In some examples, the slot 22 can have a rectangular or square cross-sectional profile. Other suitable shapes can also be used.

In some examples, the body 12 can further include a threaded hole 44 extending through the circumferential surface 30 to the slot 22. In some examples, the threaded hole 44 can extend in the second direction. In some examples, the threaded hole 44 can receive fastener, such as a set screw, to secure the slide 24 to the body 12.

In some examples, the body 12 can include a peripheral portion 46 adjacent to the circumferential surface 30. In some examples, the body 12 can further include a diametric portion 48 extending from the widest portion 32 of the circumferential surface 30 through a center of the body 12 to the narrowest portion 34 of the circumferential surface 30. In some examples, the peripheral portion 46 and the diametric portion 48 can define two apertures 50, 52 on opposite sides of the diametric portion 48. In some examples, each of the two apertures 50, 52 can extend through the wedged surfaces 14, 18. Forming the body 12 with the apertures 50, 52 can enhance bone growth through and around the body 12 over time, which can increase strength and stability of the implant. The apertures 50, 52 are but examples of apertures formed in the body 12; other suitable apertures and body 12 structures can also be used.

In some examples, the body 12 and/or the slide 24 can be formed through an additive manufacturing process, such as three-dimensional printing. Such an additive manufacturing process is well suited to form the body 12 as a single element, including the slot 22 and the circumferential surface 30 over the slot 22. In other examples, the body 12 and/or the slide 24 can be formed through a more conventional machining and/or molding process. In the more conventional manufacturing process, the body 12 can be manufactured as multiple elements that are subsequently attached. For example, the body 12 can be formed with the slot 22 as an open trench in the body 12. A cover 54 (FIG. 1) can be manufactured separately, and attached to the body 12 to cover the slot 22. An advantage to using a separate cover 54 is that the cover 54 can include the threads for the threaded hole 44. In some examples, it may be advantageous to use a relatively smooth surface finish for the cover 54, and a relatively rough surface finish for the body 12. These are but examples of manufacturing processes; other suitable manufacturing processes can also be used.

Figure 5:
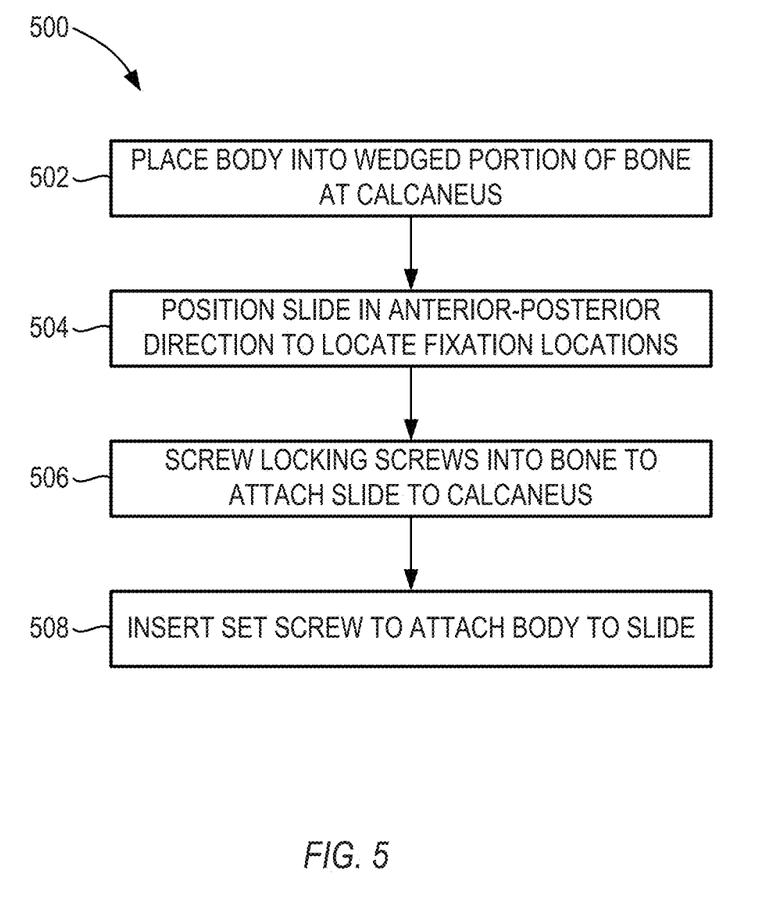
FIG. 5 shows a flowchart of a method for implanting an adjustable wedge into a corresponding wedged portion of bone on a patient's calcaneus, in accordance with some examples.

FIG. 5 shows a flowchart of a method 500 for implanting an adjustable wedge into a corresponding wedged portion of bone on a patient's calcaneus, in accordance with some examples. A surgeon can use the method to implant an adjustable wedge 10, as shown in FIGS. 1-4, or any other suitable adjustable wedge. The method 500 of FIG. 5 is but one method for implanting an adjustable wedge into a corresponding wedged portion of bone on a patient's calcaneus. Other suitable methods can also be used.

Prior to executing the method 500, a surgeon can perform an osteotomy to obtain a wedge-shaped cutout of bone on the patient's calcaneus.

At operation 502, the surgeon can place a body of the adjustable wedge into the corresponding wedged cutout of bone on the patient's calcaneus. The body can include a slot through the body. The adjustable wedge can further include a slide that is non-removably positioned in the slot and slidable within the slot. The slide can include first and second holes through the slide at opposite ends of the slide. The first and second holes can be positioned outside the slot at locations that allow the first and second holes to remain accessible over a full range of motion of the slide within the slot.

At operation 504, the surgeon can position the slide in an anterior-posterior direction on the calcaneus to locate a pair of specified screw fixation locations. The surgeon can select suitable locations based on bone geometry, bone density, bone thickness, proximity to other tissue, and other suitable factors.

At operation 506, the surgeon can screw a pair of locking screws into the bone on the patient's calcaneus at the pair of specified screw fixation locations through the first and second holes, respectively, to secure the slide to the calcaneus.

At operation 508, the surgeon can insert a set screw into a threaded hole on the body to secure the body to the slide.

To further illustrate the device and related method disclosed herein, a non-limiting list of examples is provided below. Each of the following non-limiting examples can stand on its own, or can be combined in any permutation or combination with any one or more of the other examples.

In Example 1, an adjustable wedge can include: a slide including first and second holes through the slide at opposite ends of the slide; and a body having: a pair of wedged surfaces that are angled with respect to each other; a circumferential surface extending circumferentially between the wedged surfaces; a slot extending through the body between the wedged surfaces, the slot sized to accommodate the slide so that the slide is slidable within the slot; and a threaded hole extending through the circumferential surface to the slot, the threaded hole configured to receive a fastener to secure the slide to the body.

In Example 2, the adjustable wedge of Example 1 can optionally be configured such that the slide and the slot extend along a first direction; and the slide is slidable within the slot in the first direction.

In Example 3, the adjustable wedge of any one of Examples 1-2 can optionally be configured such that the slide and the slot are shaped to prevent rotation of the slide about an axis extending along the first direction.

In Example 4, the adjustable wedge of any one of or a combination of Examples 1-3 can optionally be configured such that the slide and the slot each include opposing walls that are flat.

In Example 5, the adjustable wedge of any one of or a combination of Examples 1-4 can optionally be configured such that the first and second holes extend in a second direction perpendicular to the first direction.

In Example 6, the adjustable wedge of any one of or a combination of Examples 1-5 can optionally be configured such that the threaded hole extends in the second direction.

In Example 7, the adjustable wedge of any one of or a combination of Examples 1-6 can optionally be configured such that the pair of wedged surfaces define respective planes that intersect outside the body along a line that defines a third direction, the third direction being perpendicular to the first and second directions.

In Example 8, the adjustable wedge of any one of or a combination of Examples 1-7 can optionally be configured such that the slide extends between first and second enlarged longitudinal portions of the slide, the first and second enlarged longitudinal portions sized larger than the slot and preventing the slide from exiting the slot.

In Example 9, the adjustable wedge of any one of or a combination of Examples 1-8 can optionally be configured such that the first and second enlarged longitudinal portions surround the first and second holes, respectively.

In Example 10, the adjustable wedge of any one of or a combination of Examples 1-9 can optionally be configured such that the first and second holes are threaded.

In Example 11, the adjustable wedge of any one of or a combination of Examples 1-10 can optionally be configured such that the first hole has a first thread size and the second hole has a second thread size equal to the first thread size.

In Example 12, the adjustable wedge of any one of or a combination of Examples 1-11 can optionally be configured such that the slot is positioned proximate a widest portion of the circumferential surface.

In Example 13, the adjustable wedge of any one of or a combination of Examples 1-12 can optionally be configured such that: the body further includes a peripheral portion adjacent to the circumferential surface; the body further includes a diametric portion extending from a widest portion of the circumferential surface through a center of the body to a narrowest portion of the circumferential surface; and the peripheral portion and the diametric portion define two apertures on opposite sides of the diametric portion, each of the two apertures extending through the wedged surfaces.

In Example 14, the adjustable wedge of any one of or a combination of Examples 1-13 can optionally be configured such that the body is formed as a single integral element that defines the threaded hole.

In Example 15, the adjustable wedge of any one of or a combination of Examples 1-14 can optionally further include a cover positioned on the body, the cover defining the threaded hole, the cover having a smoother surface finish than the body.

In Example 16, an adjustable wedge can include: a slide extending along a first direction, the slide including first and second holes extending through the slide at opposite ends of the slide, the first and second holes extending in a second direction perpendicular to the first direction, the slide extending between first and second enlarged longitudinal portions of the slide, the first and second enlarged longitudinal portions surrounding the first and second holes, respectively; a body having: a pair of wedged surfaces that are angled with respect to each other, the pair of wedged surfaces defining respective planes that intersect outside the body along a line that defines a third direction, the third direction being perpendicular to the first and second directions; a circumferential surface extending circumferentially between the wedged surfaces; a slot extending through the body in the first direction between the wedged surfaces, the slot positioned proximate a widest portion of the circumferential surface, the slot sized to accommodate the slide so that the slide is slidable within the slot in the first direction, the slot sized smaller than the first and second enlarged longitudinal portions of the slide so that the first and second enlarged longitudinal portions prevent the slide from exiting the slot, the slide and the slot being shaped to prevent rotation of the slide about an axis extending along the first direction; and a threaded hole extending through the circumferential surface to the slot, the threaded hole extending in the second direction, the threaded hole configured to receive a set screw to secure the slide to the body.

In Example 17, the adjustable wedge of Example 16 can optionally be configured such that the first and second holes are threaded; and the first hole has a first thread size and the second hole has a second thread size equal to the first thread size.

In Example 18, the adjustable wedge of any one of Examples 16-17 can optionally be configured such that: the body further includes a peripheral portion adjacent to the circumferential surface; the body further includes a diametric portion extending from a widest portion of the circumferential surface through a center of the body to a narrowest portion of the circumferential surface; and the peripheral portion and the diametric portion define two apertures on opposite sides of the diametric portion, each of the two apertures extending through the wedged surfaces.

In Example 19, the adjustable wedge of any one of Examples 16-18 can optionally be configured to further include a cover positioned on the body, the cover defining the threaded hole, the cover having a smoother surface finish than the body.

In Example 20, a method for implanting an adjustable wedge into a corresponding wedged cutout of bone on a patient's calcaneus can include: placing a body of the adjustable wedge into the corresponding wedged cutout of bone on the patient's calcaneus, the body including a pair of wedged surfaces configured to contact the cutout of bone, the body including a slot extending between the wedged surfaces in an anterior-posterior direction, the adjustable wedge including a slide extending through the slot and slidable within the slot in the anterior-posterior direction; positioning the slide in the anterior-posterior direction on the calcaneus to locate a pair of specified screw fixation locations; screwing a pair of locking screws into the bone on the patient's calcaneus at the pair of specified screw fixation locations through first and second holes on the slide, respectively, to secure the slide to the calcaneus; and inserting a fastener into a threaded hole extending through a portion of the body to secure the body to the slide.

While this invention has been described as having example designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An adjustable calcaneus wedge for implantation in a resection of a patient's calcaneus, the adjustable calcaneus wedge comprising:
    a slide extending along a first direction, the slide including first and second holes through the slide at opposite ends of the slide, the first and second holes extending in a second direction perpendicular to the first direction, the slide extending between first and second enlarged longitudinal portions of the slide, the first and second enlarged longitudinal portions surrounding the first and second holes, respectively; and
    a substantially disc-shaped body having:
        a pair of wedged surfaces that are angled with respect to each other, the pair of wedged surfaces defining respective planes that intersect outside the body along a line that defines a third direction, the third direction being perpendicular to the first and second directions;
        a circumferential surface extending circumferentially between the wedged surfaces;
        a slot extending through the body in the first direction between the wedged surfaces, the slot positioned proximate a widest portion of the circumferential surface, the slot sized to accommodate the slide so that the slide is slidable within the slot in the first direction, the slot sized smaller than the first and second enlarged longitudinal portions of the slide so that the first and second enlarged longitudinal portions prevent the slide from exiting the slot, the slide and the slot being shaped to prevent rotation of the slide about an axis extending along the first direction, the slot positioned such that each wedged surface surrounds a respective end of the slot;
        a hole extending through the circumferential surface to the slot, the hole configured to receive a fastener to secure the slide to the body;
        a peripheral portion adjacent to the circumferential surface; and
        a diametric portion extending from a first portion of the circumferential surface through a center of the body to a second portion of the circumferential surface, the peripheral portion and the diametric portion defining two apertures within the body.

2. The adjustable calcaneus wedge of claim 1, wherein the slide and the slot each include opposing walls that are flat.

3. The adjustable calcaneus wedge of claim 1, wherein the hole extending through the circumferential surface extends in the second direction.

4. The adjustable calcaneus wedge of claim 1, wherein the first and second enlarged longitudinal portions surround the first and second holes, respectively.

5. The adjustable calcaneus wedge of claim 1, wherein the first and second holes are threaded.

6. The adjustable calcaneus wedge of claim 5, wherein the first hole has a first thread size and the second hole has a second thread size equal to the first thread size.

7. The adjustable calcaneus wedge of claim 1, wherein:
    the diametric portion extends from a widest portion of the circumferential surface through the center of the body to a narrowest portion of the circumferential surface; and
    each of the two apertures extending through the wedged surfaces.

8. The adjustable calcaneus wedge of claim 1, wherein the body is formed as a single integral element that defines the threaded hole.

9. The adjustable calcaneus wedge of claim 1, further comprising a cover positioned on the body, the cover defining the hole extending through the circumferential surface, the cover having a smoother surface finish than the body.

10. The adjustable calcaneus wedge of claim 1, wherein the hole extending through the circumferential surface is threaded.

11. An adjustable calcaneus wedge for implantation in a resection of a patient's calcaneus, the adjustable calcaneus wedge comprising:
- a slide extending along a first direction, the slide including first and second holes extending through the slide at opposite ends of the slide, the first and second holes extending in a second direction perpendicular to the first direction, the slide extending between first and second enlarged longitudinal portions of the slide, the first and second enlarged longitudinal portions surrounding the first and second holes, respectively; and
- a substantially disc-shaped body having:
  - a pair of wedged surfaces that are angled with respect to each other, the pair of wedged surfaces defining respective planes that intersect outside the body along a line that defines a third direction, the third direction being perpendicular to the first and second directions;
  - a circumferential surface extending circumferentially between the wedged surfaces;
  - a slot extending through the body in the first direction between the wedged surfaces, the slot positioned proximate a widest portion of the circumferential surface, the slot sized to accommodate the slide so that the slide is slidable within the slot in the first direction, the slot sized smaller than the first and second enlarged longitudinal portions of the slide so that the first and second enlarged longitudinal portions prevent the slide from exiting the slot, the slide and the slot being shaped to prevent rotation of the slide about an axis extending along the first direction;
  - a threaded hole extending through the circumferential surface to the slot, the threaded hole extending in the second direction, the threaded hole configured to receive a set screw to secure the slide to the body;
  - a peripheral portion adjacent to the circumferential surface; and
  - a diametric portion extending from a first portion of the circumferential surface through a center of the body to a second portion of the circumferential surface, the peripheral portion and the diametric portion defining two apertures within the body.

12. The adjustable calcaneus wedge of claim 11, wherein:
the first and second holes are threaded; and
the first hole has a first thread size and the second hole has a second thread size equal to the first thread size.

13. The adjustable calcaneus wedge of claim 11, wherein:
the diametric portion extends from a widest portion of the circumferential surface through the center of the body to a narrowest portion of the circumferential surface; and
each of the two apertures extending through the wedged surfaces.

14. The adjustable calcaneus wedge of claim 11, further comprising a cover positioned on the body, the cover defining the threaded hole, the cover having a smoother surface finish than the body.

* * * * *